Jan. 20, 1959 V. R. JAMES Plant Pat. 1,801
CAMELLIA PLANT
Filed June 3, 1958
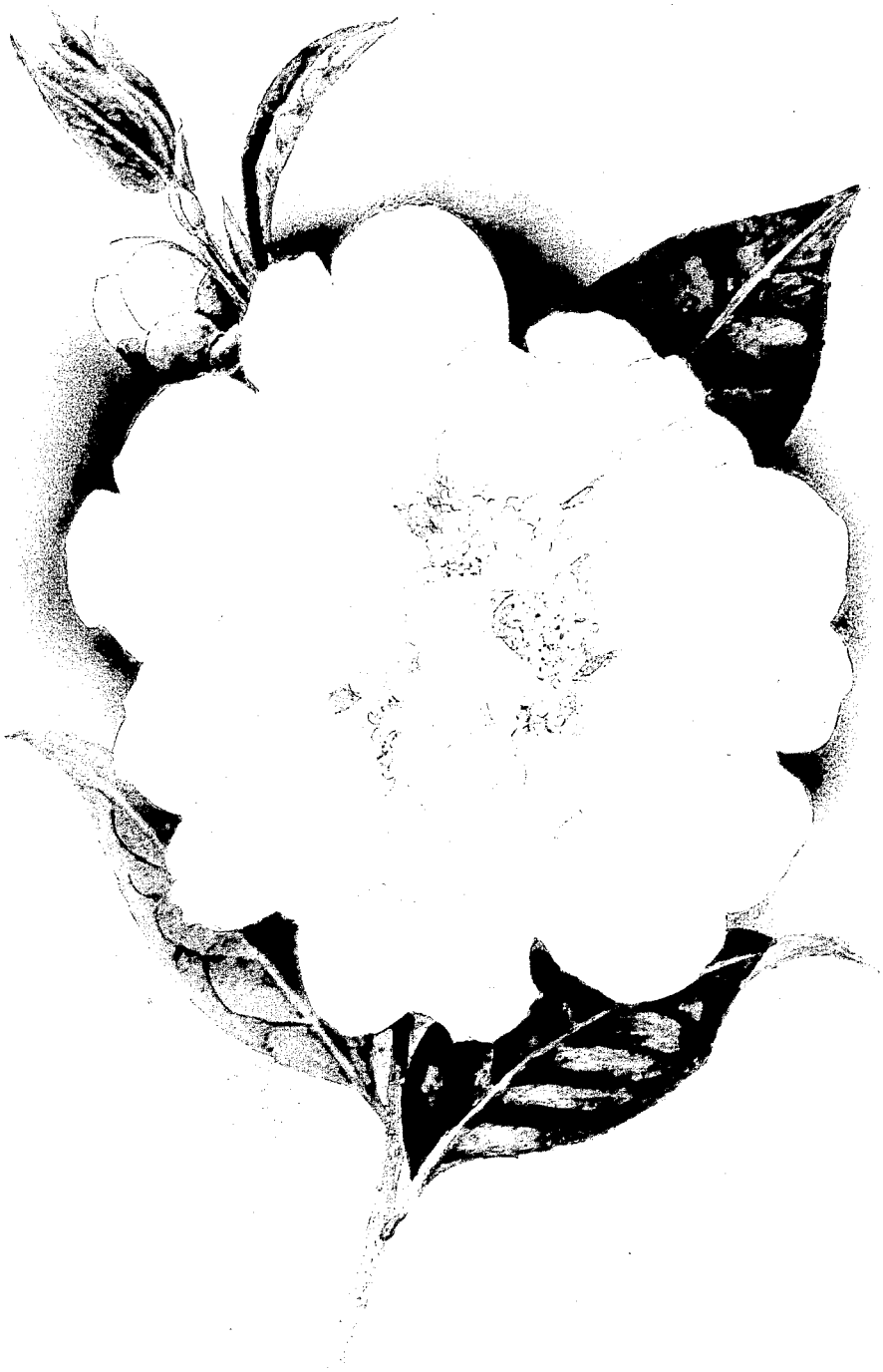
WITNESS
Gadison E. Avery
INVENTOR
VERNON R. JAMES
by Rummler & Snow
ATTYS.

United States Patent Office

Plant Pat. 1,801
Patented Jan. 20, 1959

1,801

CAMELLIA PLANT

Vernon R. James, Aptos, Calif.

Application June 3, 1958, Serial No. 739,644
1 Claim. (Cl. 47—60)

My present invention concerns a new and distinct variety of camellia plant which was developed by me on my breeding plot in Los Gatos, California, through a succession of crosses that were pollinated in planned direction since 1950, the immediate seed parent being Clone Cuspidata × Saluenensis and the pollen parent Hybrid Clone × Japonica, both unpatented. Propagation of this new variety is at the present time being carried on in Aptos, California. This new variety of camellia has been asexually reproduced through several generations, at Aptos, California, by cuttings and by grafting and the progeny of this new variety have continued to come true to form in all respects, thereby perpetuating the novel characteristics.

The primary object in carrying out my breeding efforts was to develop a camellia plant having a flower of larger size with an intense, warm pink color and improved characteristics of floriferousness and hardiness to cold weather. These results have now been obtained and fixed in the present new variety.

The accompanying illustration shows in full color a typical full-blown blossom, bud and the leaves.

The following is a detailed description of the new variety:

Parentage: Seedling.
*Seed parent.*—Clone Cuspidata × Saluenensis.
*Pollen parent.*—Hybrid Clone × Japonica.
Botanic name: Saluenensis Hybrid.

*Flower*

Blooming habit: Recurrent. Blooms profusely from early January through April.
Size: Large—4 to 4½ inches in diameter. Depth—2 to 3 inches.
Borne: Singly.
Shape: Fluted, semi-double to Anemone form. When bloom first opens it is cup-shaped, with a high center. Later guard petals form and the bloom flattens out horizontally.
Petalage:
*Number.*—10.
*Arrangement.*—Imbricated.
*Color.*—Outer petals—Phlox pink. Base—a shade deeper. Inside petals—Phlox Pink. Reverse side—Phlox Pink.
*Texture.*—Leathery with satiny appearance.
*Lasting quality on stem.*—12 to 16 days.
Petalettes:
*Number.*—25 (average).
*Size.*—2¾ in. x 1½ inches.
Petaloids:
*Number.*—20 to 30 (average).
*Size.*—⅛ x ⅛ inch to ¼ x ⅜ inch.
Stamens: 125 to 135.
Lasting quality of flower: 12 to 16 days on plant; 4–5 days as a cut flower, depending upon ambient humidity; 5 days in an open dish. Flowers drop clean and are not affected by wet or hot weather.
Discoloration after full bloom: None.

*Bud*

Shape: Ovoid.

Diameter: 1¾ to 2½ inches (at color stage).
Depth: 1 to 2 inches (at color stage). Opens slowly.
Color: Phlox Pink when sepals first divide and when petals begin to unfurl.
Sepals: Hooded over bud. Fastened together at base.
Calyx: Cupped shape, with smooth and slightly hairy aspect.
Peduncle: None.

*Plant*

Form: Bush. Upright, vigorous and strong.
Height: Grows to about 20 feet in approximately 40 years.
Foliage: Abundant.
*Size of leaf.*—3½ x 1⅝ inches.
*Color of leaf.*—Upper side—Dark Green. Under side—Light Green.
Petioles: Length—½ inch.
Ribs and veins: Indented.
Genital organs:
*Stamens.*—Anthers: number—125–135; length—1/16 inch. Filaments: length—1¼ to 1½ inches; color—Pale Green.
*Pollen.*—Golden Yellow.
*Pistils.*—Number—1. Length—1 to 1¼ inches. Stigmas—Pale Green in color.
*Ovaries.*—Sterile.
Fruit: Sterile.

The color designations according to British Color Council Horticultural Color Chart are as follows:

| | Sheet | Color | Number |
|---|---|---|---|
| Flower: | | | |
| Lightest shade: Inside and reverse side shading to same color, 2 shades darker especially at base | 77 | Phlox Pink | 625/3 |
| Stigmas and filaments | 90 | Chartreuse Green. | 663/2 |
| Stamens—anthers | 3 | Aureolin | 3/2 |
| to | 5 | Buttercup Yellow. | 5/1 |

Color designations according to "A Dictionary of Color by Maerz and Paul":

| | Plate | Letter | No. |
|---|---|---|---|
| Face of leaf | 23 | L | 7-plus yellow. |
| Under side of leaf | 21 | L | 6. |

Referring to the novel characteristics of this new variety, in comparison to other Saluenensis Hybrids, the flower is larger in size, more double, and is distinctive in its unique pink coloring, with each petal having delicate-lavender, vein-like lines running from the apex toward the base and a transparent character that gives the flower an appearance of great depth. Other distinctions of the new variety are the profuseness of blooming; with buds forming singly along the stem and usually with two buds at the tip of the branch; the fact that the flowers drop free and do not dry on the bush, after being open about 12 to 16 days; and the flower structure wherein the guard petals lay out flat when the flower is fully opened and the mixed petalettes and petaloids, together with the stamens, stand upright but flare outwardly to provide the flower with a fluted center.

Having thus disclosed the invention, I claim:

A new and distinct variety of camellia plant, substantially as shown and described, characterized particularly by its floriferousness, the distinctive pink coloring of the boom, the large size of the bloom, its hardiness to cold weather, and its vigorous strong growth.

No references cited.